United States Patent [19]
Matsumoto et al.

[11] Patent Number: 5,618,993
[45] Date of Patent: Apr. 8, 1997

[54] ULTRASONIC DETECTION APPARATUS AND METHOD FOR DETECTING ACOUSTIC EMISSION

[75] Inventors: Kazuo Matsumoto; Haruhiko Ueno; Kenji Shimada, all of Higashimatsuyama, Japan

[73] Assignee: Zexel Corporation, Tokyo, Japan

[21] Appl. No.: 575,467

[22] Filed: Dec. 20, 1995

Related U.S. Application Data

[63] Continuation of Ser. No. 347,126, Nov. 23, 1994, abandoned.

[30] Foreign Application Priority Data

Dec. 24, 1993 [JP] Japan ................................. 5-347370

[51] Int. Cl.$^6$ ................................................... G01H 1/00
[52] U.S. Cl. ..................... 73/587; 73/593; 73/660
[58] Field of Search ..................... 73/587, 660, 593, 73/644, 801; 340/680, 683; 451/21, 22; 125/11.01; 408/8

[56] References Cited

U.S. PATENT DOCUMENTS

| | | | |
|---|---|---|---|
| 3,420,097 | 1/1969 | Battermann et al. | 73/644 |
| 4,530,246 | 7/1985 | Pitman et al. | 73/799 |
| 4,744,348 | 5/1988 | Oda et al. | 451/26 |
| 4,821,460 | 4/1989 | Wegmann | 451/26 |
| 5,485,752 | 1/1996 | Asano et al. | 73/587 |

FOREIGN PATENT DOCUMENTS

| | | | |
|---|---|---|---|
| 28451 | 2/1983 | Japan | 340/680 |
| 140058 | 6/1989 | Japan | 73/587 |
| 90057 | 3/1990 | Japan | 73/587 |
| 28733 | 2/1991 | Japan | 73/587 |
| 1523992 | 11/1989 | U.S.S.R. | 73/587 |

OTHER PUBLICATIONS

Translation of JP 140058.
Translation of JP 90057.

*Primary Examiner*—Hezron E. Williams
*Assistant Examiner*—Nashmiya Ashraf
*Attorney, Agent, or Firm*—Sughrue, Mion, Zinn, Macpeak & Seas

[57] ABSTRACT

An apparatus in which ultrasonic vibrations or acoustic emissions are detected includes a rotating shaft 21 having a dressing wheel 31 mounted on one end, and a detection liquid supply unit 41 disposed at the end face of the wheel and/or shaft so as to form a gap S therebetween and to supply detection liquid toward the rotational center of the wheel to form a detection liquid membrane in the gap. An AE sensor 43 is provided integrally with the detection liquid supply unit and detects the ultrasonic vibrations or acoustic emissions of the wheel and/or shaft through the detection liquid membrane formed in the gap.

7 Claims, 6 Drawing Sheets

ULTRASONIC DETECTION APPARATUS AND METHOD FOR DETECTING ACOUSTIC EMISSION

This is a Continuation of application Ser. No. 08/347,126 filed Nov. 23, 1994 now abandoned.

BACKGROUND OF THE INVENTION

1. Field of the Invention

This invention relates to an ultrasonic detection apparatus, and to a method for detecting ultrasonic vibration or acoustic emission (AE) produced by a high-speed rotating member in a non-contact manner.

2. Description of the Related Art

A rotary dressing apparatus has been used to shape a grinding wheel (stone) for grinding workpieces. This type of rotary dressing apparatus generally includes a housing, a dresser shaft which is rotatably supported in the housing, and a dresser which has a cutting edge of diamonds or the like at the tip portion thereof and is mounted to the end portion of the dresser shaft. In use, the dresser is contacted with a rotating grinding wheel while rotating the dresser shaft to thereby shape the surface of the grinding wheel.

In order to enhance the efficiency of a shaping process, it is required to minimize contact (grinding allowance) between the dresser and the grinding wheel. This requirement is somewhat satisfied by an operator relying on his hearing to detect the noise produced when the dresser wheel contacts the grinding wheel. However, such human detection is low in accuracy and is generally accompanied by substantial error.

In order to enhance the grinding-wheel shaping precision, reduce loss of abrasive grains, improve the use efficiency of the grinding wheel and reduce the grinding cost, the contact between the dresser and the grinding wheel is required to be automatically detected in an electrical or mechanical manner. In order to satisfy this requirement, for example, U.S. Pat. No. 4,744,348 (Japanese Utility Model publication No. 64-278) discloses an ultrasonic detection apparatus having an ultrasonic or AE sensor for detecting ultrasonic vibrations or acoustic emissions produced when the dresser is contacted with the grinding wheel, thereby automatically detecting the contact between the dresser and the grinding wheel without human detection.

In the ultrasonic detection apparatus as disclosed in these publications (as shown in FIG. 10), an AE sensor 61 is provided integrally with a housing (supporter) 63 for supporting a dresser 62 serving as a rotator, and a cutting (detection) liquid is supplied from a detection liquid supply unit 64 into a gap between the rotating dresser 62 and the housing 63 to form a liquid membrane in the gap. The ultrasonic vibration (AE) produced when the cutting edge 65 of the dresser 62 is contacted with the grinding wheel is transmitted through the liquid membrane and the housing 63 to the AE sensor 61 to detect the contact between the dresser and the grinding wheel with a resolution of in the micron range.

FIG. 11 shows a cross-sectional view of the ultrasonic detection apparatus shown in FIG. 10, and shows an arrangement of the detection liquid supply unit 64. As shown in FIG. 11, the detection liquid supply unit 64 for supplying the detection liquid into the gap between the rotating dresser 62 and the housing 63 is disposed away from the rotational axis of the dresser, and it supplies the detection liquid from such a position into the gap. Therefore, the liquid membrane 66 is radially spread around the rotational axis in a doughnut shape. When the dresser 62 rotates at a high speed, the doughnut-shaped liquid membrane 66 is greatly scattered from the peripheral surface of the dresser 62 due to centrifugal force, and thus the liquid membrane cannot be evenly formed in the gap. Therefore, the transmission of the ultrasonic vibration through the liquid membrane to the AE sensor 61 is disturbed, and thus high precision cannot be obtained for detection of the ultrasonic vibrations as shown in FIG. 9.

FIG. 9 is a graph showing a measurement result of an output N with respect to a supply voltage S when the rotator was rotated at a high speed of 5000 rpm. In FIG. 9, the abscissa represents time SEC in seconds and the ordinate represents an effective voltage V (volt). An S/N was calculated on the basis of the above measurement result to be 3.5. In general, the detection sensitivity of the AE sensor is good when the S/N exceeds 5, and thus the conventional ultrasonic detection apparatus as described above has a low sensitivity.

SUMMARY OF THE INVENTION

An object of the present invention is to provide an ultrasonic detection apparatus having high measuring precision in which an excellent liquid membrane can be formed without being effected by centrifugal force even when a rotator is rotated at a high speed.

In order to attain the above object, according to a first aspect of the present invention, an ultrasonic detection apparatus for detecting ultrasonic vibration or acoustic emission (AE) produced by a rotator, includes a rotator serving as a detection target, a detection liquid supply unit which is disposed away from the rotator so as to form a gap therebetween and supplies detection liquid toward the rotational center of the rotator to form a detection liquid membrane in the gap, and an AE sensor which is provided integrally with the detection liquid supply unit and detects the ultrasonic vibration or acoustic emission of the rotator through the detection liquid membrane formed in the gap.

According to the ultrasonic detection apparatus of the first aspect of the present invention, the detection liquid is supplied from the detection liquid supply unit to the rotational center of the rotator, and thus the detection liquid membrane formed on the surface of the rotator is hardly affected by centrifugal force, even when the rotator is rotated at a high speed. Accordingly, scattering of the detection liquid from the liquid membrane and reduction in area of the membrane can be suppressed, and thus an excellent liquid membrane can be formed.

The ultrasonic vibrations acoustic emissions produced when the dresser and the grinding wheel contact each other are transmitted through the liquid membrane thus formed and then detected by the AE sensor.

The liquid membrane can be formed so as to be little affect by centrifugal force even when the rotational speed is high, and thus the rotator can be rotated at a higher speed than the prior art.

Further, according to a second aspect of the present invention, an ultrasonic detection apparatus for detecting ultrasonic vibrations or acoustic emissions produced by a rotator includes a detection liquid supply unit for supplying detection liquid toward the rotational center of the rotator, a detection plate which is disposed away from the rotator serving as a detection target and serving to keep a liquid membrane in a gap between the rotator and the detection plate, and an AE sensor which is provided integrally with the detection plate and detects ultrasonic vibration of the rotator through the detection liquid membrane formed by the detection liquid supplied into the gap.

According to the ultrasonic detection apparatus of the second aspect of the present invention, the AE sensor and the supporter for supporting the rotator are provided separately from each other, so that the AE sensor is not affected by the vibration of the supporter, and thus the measuring precision can be improved over the first aspect.

The ultrasonic detection apparatus of the present invention is provided separately from the rotator, so that only a single ultrasonic detection apparatus can be easily applied to various kinds of rotators. In this case, it is unnecessary to secure the ultrasonic detection apparatus to the rotator, so that the construction of the rotator can be simplified.

According to a third aspect of the invention, an ultrasonic detection method for detecting ultrasonic vibration or acoustic emissions produced by a rotator comprises the steps of disposing a detection plate so as to face a surface of a rotator which contains a rotational center, supplying detection liquid toward the rotational center of the rotator serving as a detection target, forming a detection liquid membrane in a gap between the rotator and the detection plate, and detecting ultrasonic vibrations or acoustic emissions produced by the detection liquid membrane by an AE sensor.

According to the ultrasonic detection method of the third aspect of the present invention, the detection liquid is supplied toward the rotational center of the rotator in the detection liquid supply step, so that the detection liquid membrane formed on the surface of the rotator is little affected by centrifugal force even at high-speed rotation. Accordingly, the scattering of the detection liquid from the liquid membrane and the reduction in area of the membrane can be suppressed, so that an excellent detection liquid membrane can be formed.

DETAILED DESCRIPTION OF THE PREFERRED EMBODIMENTS

Preferred embodiments according to the present invention will be described with reference to FIGS. 1 to 8.

First, a dressing apparatus 1 used in a first embodiment will be described.

Figure 1:
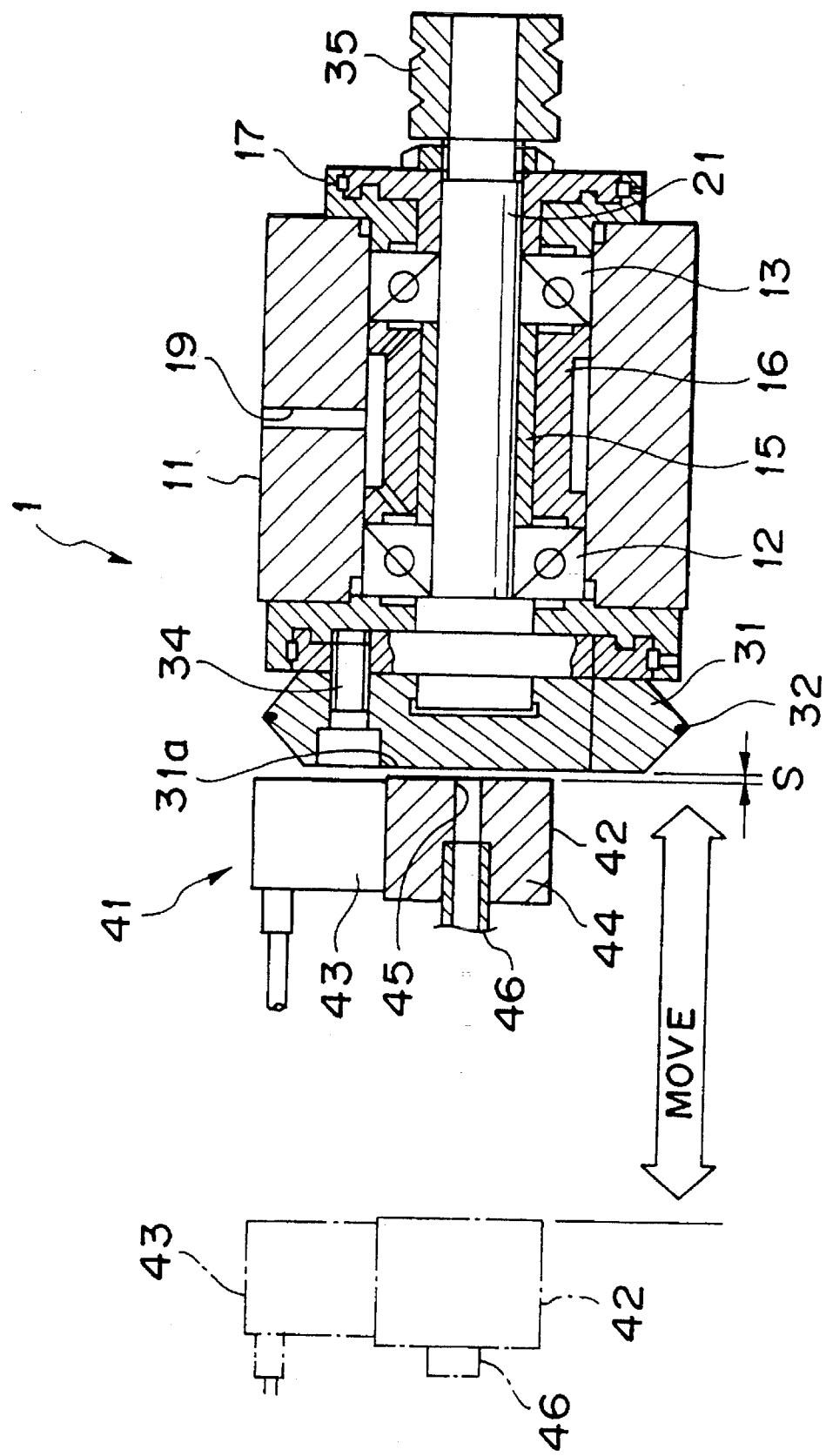
FIG. 1 schematically shows an ultrasonic detection apparatus according to a first embodiment of the present invention.

In FIG. 1, the dressing apparatus 1 includes a housing 11, a dresser shaft 21 which is rotatably mounted in the housing 11 through bearings 12 and 13, and a dresser 31 which is detachably mounted to the left end of the dresser shaft 21 projecting from the housing 11. The dressing apparatus 1 is designed so that the shaping of the surface of a grinding wheel is performed by contacting the dresser with the grinding wheel.

An inner sleeve 15 and an outer sleeve 16 are interposed between the bearings 12 and 13 in the housing 11, and mounted in the housing 11 so that the dresser shaft 21 is rotatable, but not movable in the axial direction.

In the housing 11 is formed an oil supply path 19 through which lubricant oil mist is supplied to the bearings 12 and 13 and into a gap between the inner and outer sleeves 15 and 16. The supply path 19 is supplied with the lubricant oil mist from a lubricant supply source (not shown).

Further, a cover plate 17 is mounted to the right end of the housing 11.

The dresser 31 serving as the rotator which has a cutting edge 32 of diamond or the like is fixed to the end of the dresser shaft 21 by a nut 34. Further, a pulley 35 is linked to the right end of the dresser shaft 21, and it is further linked to a drive shaft of a drive power source through a pulley belt (not shown) of the drive shaft.

Figure 2:
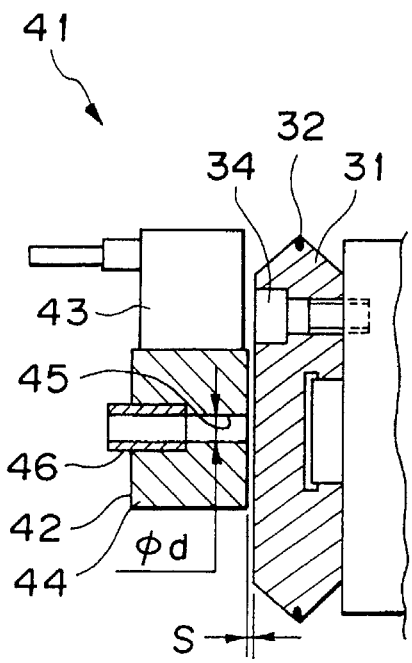
FIG. 2 is a cross-sectional view of a main part of the ultrasonic detection apparatus shown in FIG. 1.

Next, the ultrasonic detection apparatus 41 of the first embodiment will be described with reference to FIGS. 1 and 2.

Unlike the conventional ultrasonic detection apparatus, the ultrasonic detection apparatus 41 of the first embodiment is provided separately from the dressing apparatus as described above, and it is disposed away from the planar front face 31a of the dresser 31 of the dressing apparatus 1 at a predetermined interval S. It is supported by a support member (not shown) so as to be movable along the axial direction of the dresser shaft (as indicated by an arrow in FIG. 1).

The ultrasonic detection apparatus 41 includes a detection liquid supply unit 42 for supplying detection liquid to the rotational center of the front face 31a of the dresser 31 serving as the rotator, and an AE sensor 43 which is provided integrally with the detection liquid supply unit 42.

The detection liquid supply unit 42 has a detection plate 44. An oil feed hole (detection liquid supply path) 45 through which the detection liquid is injected to the rotational center of the front face 31a of the dresser 31 is formed in the detection plate 44. The oil feed hole 45 is connected to a detection liquid supply source (not shown) through a conduit 46. A low viscosity oil may be used as the detection liquid.

The AE sensor 43 is fixed to the side portion of the detection plate 44 to detect the ultrasonic vibration which is transmitted through the detection liquid membrane and the detection plate 44. In this embodiment, since the ultrasonic detection apparatus 41 is designed to be separate from the dressing apparatus, the dressing apparatus 1 is more simplified in construction and the ultrasonic detection apparatus 41 hardly suffers an effect (noise) of ultrasonic vibration produced by the dressing apparatus itself, resulting in an improvement of the measuring precision. In addition, no work and no instrument for securing and detaching the dresser 31 are required, and thus management for instruments can be facilitated.

The AE sensor 43 is a well-known element, wherein ultrasonic vibration is converted to an electrical signal with a piezoelectric element and then amplified with an amplifier. The amplified signal is input to a filter circuit in a monitor to remove noise components. The noise-removed signal is detected in an average-value detection circuit and then compared with a set value in an identifying circuit to judge whether the dresser and the grinding wheel are in contact each other. The judgment or identification of "contact" is made if the signal exceeds the set value. Further, when an integration value of time which exceeds a value representing a disc level is coincident with a predetermined time (dress time=feed time× width of grinding wheel), the grinding wheel is judged to be flatly dressed.

Next, the operation of the ultrasonic detection apparatus of the first embodiment will be described.

When a grinding wheel is required to be shaped due to abrasion of the grinding surface of the grinding wheel, the dressing apparatus of the first embodiment is used to shape the grinding wheel while rotating both the grinding wheel and the dresser 31.

The dressing operation of the surface of the grinding wheel by the cutting edge 32 is started at the instant when the edge 32 of the rotating dresser 31 contacts the peripheral surface of the grinding wheel, and a cut-in dimension of the dressing (a cut amount of the grinding wheel by the dresser) is managed from the above start time. That is, it is important in the dressing operation to accurately detect the time when the edge 32 of the dresser 31 contacts with the peripheral surface of the grinding wheel. In this embodiment, the contact time as described above is automatically detected by the AE sensor 43.

In the ultrasonic detection apparatus 41, the detection liquid from a detection liquid supply source (not shown) is fed from the oil feed hole 45 into the planar, uniformly with gap S between the dresser 31 and the detection plate 44. Through the supply of the detection liquid, a liquid membrane is formed of the detection liquid in the gap S between the rotating dresser 31 and the detection plate 44. In this case, the oil feed hole 45 is disposed so as to face the rotational center of the front face 31a of the dresser 31 serving as the rotator, and the detection liquid injected from the oil feed hole 45 to the rotational center forms the liquid membrane in the neighborhood of the rotational center of the dresser 31. Therefore, the liquid membrane thus formed is hardly effected by centrifugal force due to the rotation of the dresser 31. Accordingly, the scattering of the detection liquid of the liquid membrane and the reduction in area of the liquid membrane can be prevented even at high-speed rotation. In the prior art, the effect of the centrifugal force increases and thus the detection liquid membrane is more deteriorated as the peripheral speed of the dresser 31 increases. On the other hand, in this embodiment, the liquid membrane can be excellently and sufficiently formed at all times irrespective of the peripheral speed of the dresser 31 because the liquid membrane is formed at the rotational center which is not effected by centrifugal force. Accordingly, the peripheral speed of the dresser 31 can be increased above that of the prior art.

In order to keep a sufficient amount of detection liquid in the gap S, the gap S and the diameter d of the oil feed hole 45 are set to satisfy the following equation:

$$\pi d^2/4 > \pi d S \qquad (1)$$

Figure 3:
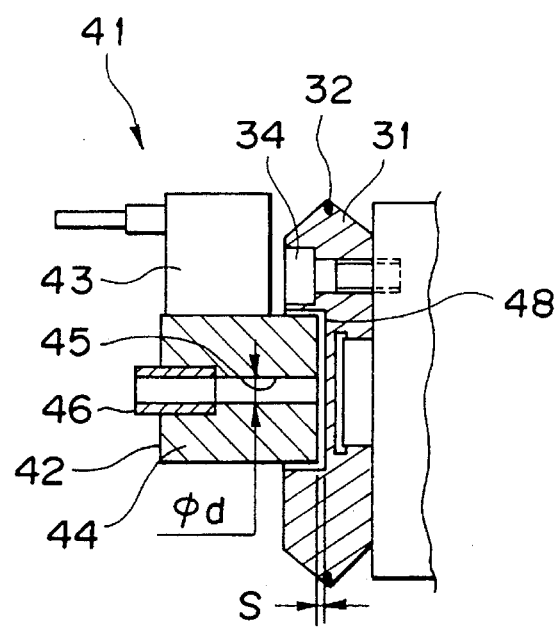
FIG. 3 is a cross-sectional view of a main part of an ultrasonic detection apparatus according to a second embodiment of the present invention.

In a second embodiment shown in FIG. 3, in order to keep the detection liquid in the gap S, a recess 48 is formed on the front face 31a of the dresser 31, and the tip of the detection plate 44 is inserted into the recess 48.

The gap S, the diameter $d_1$ of the detection plate and the inner diameter $d_2$ of the recess 48 are set to satisfy the following equation:

$$\pi d^2/4 > \pi d S > (\pi d_2^2 - \pi d_1^2)/4$$

By setting the parameters according to equation (2), the detection liquid can be effectively kept or trapped in the gap S, so that the dressing operation can be performed at a higher speed.

Figure 4:
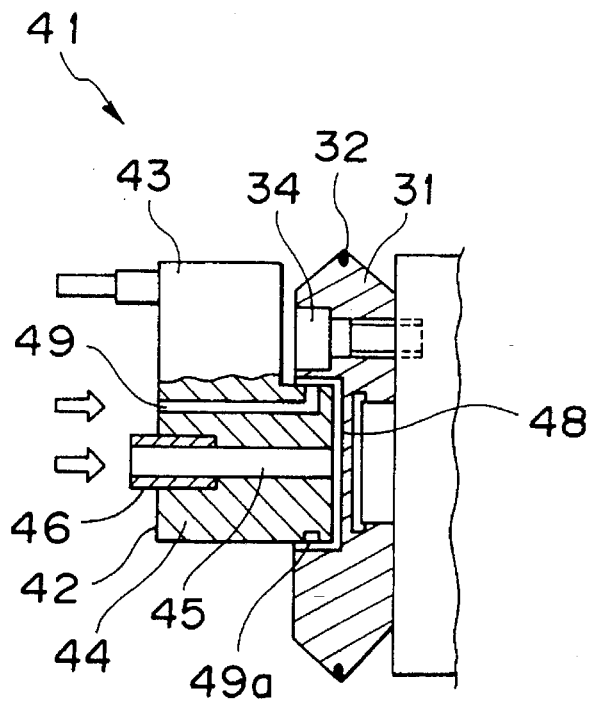
FIG. 4 is a cross-sectional view of a main part of an ultrasonic detection apparatus according to a third embodiment of the present invention.

In a third embodiment shown in FIG. 4, the detection liquid is more effectively retained by an air seal in addition to the recess the second embodiment. That is, an air path 49 through which air is passed and blown out is provided at the tip of the detection plate 44. The air path 49 has an opening 49a which faces the side surface of the recess 48, and the air seal is established by the air blown out through the opening.

Figure 5:
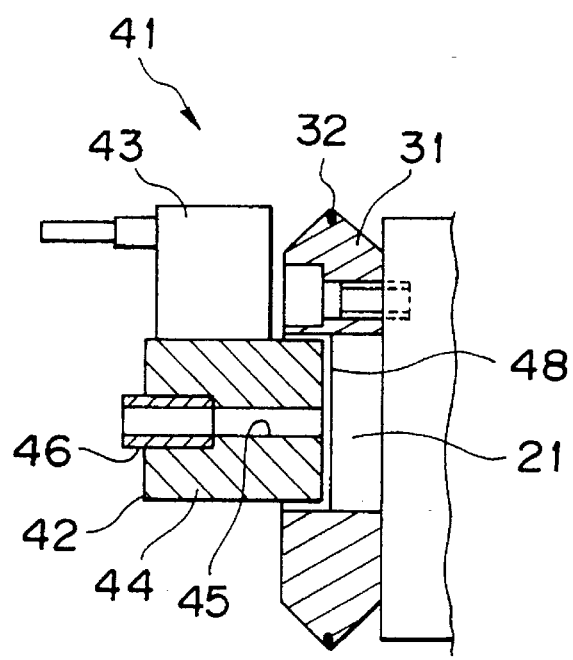
FIG. 5 is a cross-sectional view of a main part of an ultrasonic detection apparatus according to a fourth embodiment of the present invention.

In a fourth embodiment shown in FIG. 5, the detection plate 44 is disposed so as to face both the dresser 31 and the dresser shaft 21, thereby detecting the ultrasonic vibration of both the dresser the shaft. That is, the dresser 31 is designed in a doughnut shape so that the dresser shaft 21 can be disposed in the center hole of the dresser 31, and the detection plate 44 is disposed so as to face the dresser shaft 21.

Figure 6:
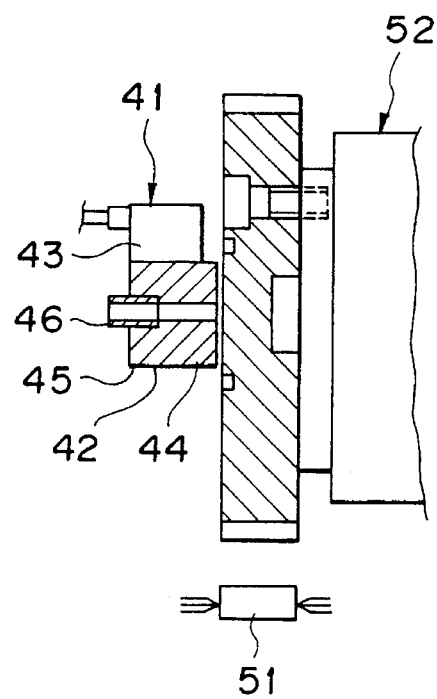
FIG. 6 is a cross-sectional view of a main part of an ultrasonic detection apparatus according to a fifth embodiment of the present invention.

In a fifth embodiment shown in FIG. 6, the ultrasonic detection apparatus 41 is applied to a grinder 52 having a grinding wheel for polishing a workpiece 51 to be processed. That is, when the ultrasonic detection apparatus 41 is provided separately from the dressing apparatus or the like, it is easily applicable to another apparatus.

Next, the effect of the embodiments as described above will be described with reference to FIGS. 7 and 8.

Figure 7:
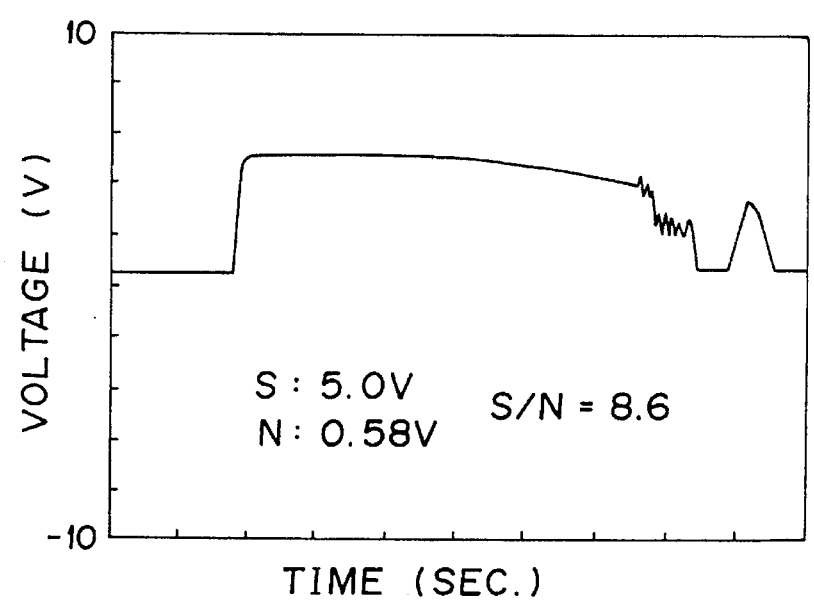
FIG. 7 is a graph showing a test result using the ultrasonic detection apparatus of the fourth embodiment according to the present invention.

A test for estimating the sensitivity of the AE sensor was performed for the fourth embodiment using the dressing apparatus shown in FIG. 5, and the test result is shown in FIG. 7.

Figure 8:
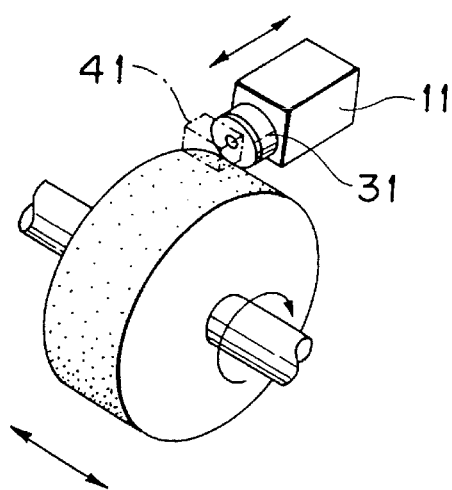
FIG. 8 is a schematic view showing a test method for the ultrasonic detection apparatus of the present invention.
Figure 9:
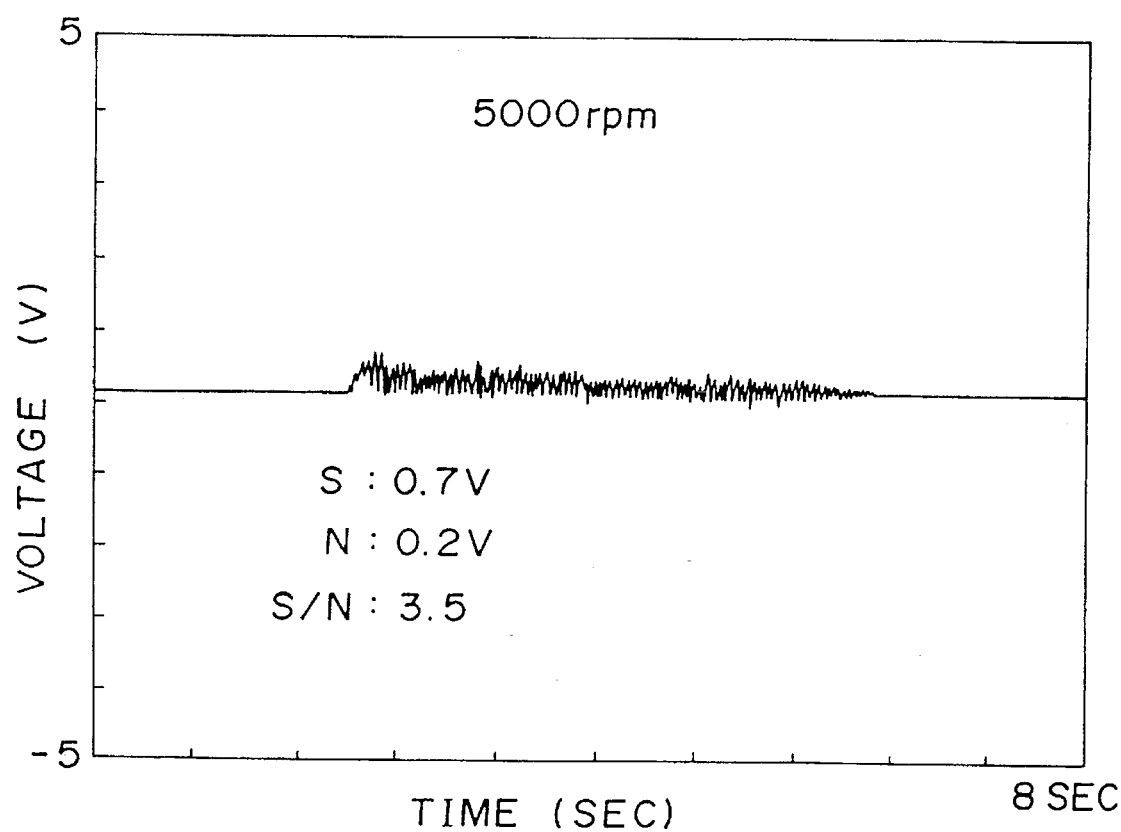
FIG. 9 is a graph showing a test result using a conventional ultrasonic detection apparatus.
Figure 10:
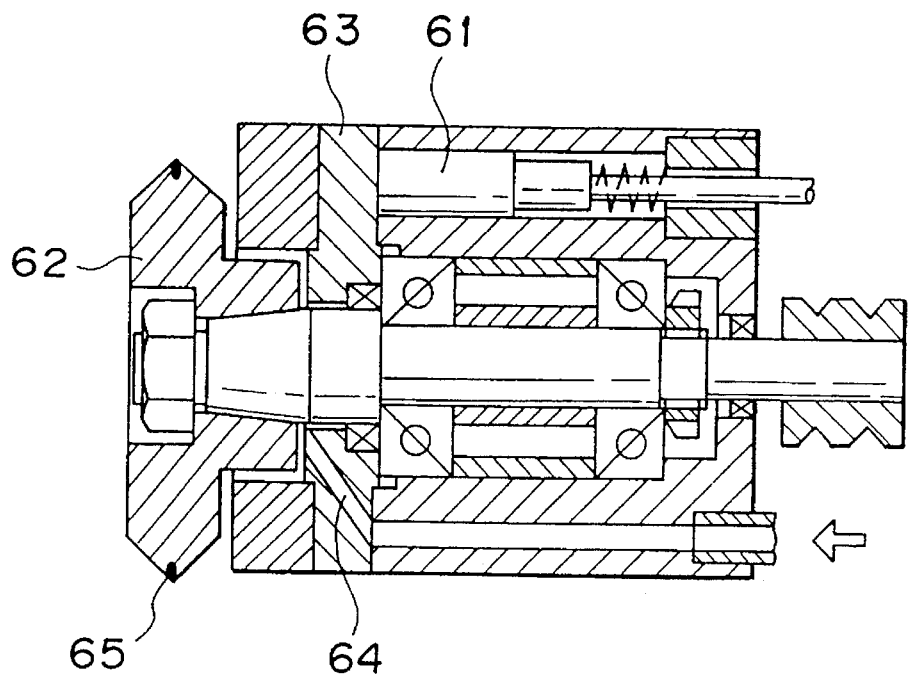
FIG. 10 is a cross-sectional view of a dressing apparatus equipped with the conventional ultrasonic detection apparatus.
Figure 11:
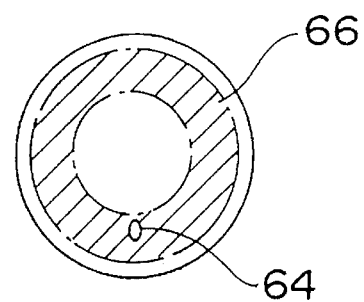
FIG. 11 is a plan view showing a liquid membrane state of the conventional ultrasonic detection apparatus shown in FIG. 10.

In the sensitivity estimating test, the cutting (dressing) process was continuously performed in such a cutting state as shown in FIG. 8, and the ultrasonic detection result at that time is shown in the graph of FIG. 7.

In FIG. 7, the abscissa represents time SEC (seconds) and the ordinate represents an effective voltage V (volts), and the output S of the AE sensor and the rotation noise output N at the time when a dresser was contacted with a grinding wheel were measured. On the basis of the measured values, the ratio of signal to noise (S/N ratio) was calculated as shown in FIG. 7. If the S/N ratio is above 5, the sensitivity is generally estimated as being good. In the test shown in FIG. 7, the S/N ratio is equal to 8.6 at a rotational speed of 5000 rpm, and it is apparent that the sensitivity of the ultrasonic detection apparatus is good. Particularly, the S/N ratio exceeds 8 and thus it is estimated that sufficient ultrasonic detection sensitivity can be obtained even at a rotational speeds above 6000 rpm.

This invention is not limited to the above embodiments, and various modifications may be made without departing from the subject matter of this invention.

For example, the ultrasonic detection apparatus of this invention is applicable to the detection of ultrasonic vibration, not only for the flat dressing of a grinding wheel, but also the centering of a lathe, detection of abnormality of a motor shaft or screw, etc. That is, the same effect of the embodiments as described above can be obtained insofar as the apparatus is applied to the detection of ultrasonic vibration (wave) of a rotator.

What is claimed is:

1. An ultrasonic detection apparatus (41) for detecting physical contact between a rotating member (21, 31) and a workpiece, comprising:

a) a detection liquid supply unit (42) having a planar end surface disposed closely adjacent a planar end face portion of said rotating member so as to form a small, planar, uniformly wide gap (S) there between, for supplying a detection liquid directly through a central portion of said planar end surface to a center of rotation of said rotating member to form a disc shaped detection liquid membrane locally in the gap, proximate to and including said center of rotation; and b) an acoustic emission sensor (43) integrally affixed to said detection liquid supply unit for detecting ultrasonic vibrations or acoustic emissions transmitted through the detection liquid membrane formed in the gap, and vibrations or emissions generated by physical contact between the rotating member and the workpiece, c) wherein Said rotating member comprises a dressing wheel of a dressing apparatus which has a cutting edge (32) on a periphery thereof for shaping a surface of a grinding wheel.

2. An ultrasonic detection apparatus (41) for detecting physical contact between a rotating member (21, 31) and a workpiece, comprising:

a) a detection liquid supply unit (42) having a planar end surface disposed closely adjacent a planar end face portion of said rotating member so as to form a small, planar, uniformly wide gap (S) therebetween, for supplying a detection liquid directly through a central portion of said planar end surface to a center of rotation of said rotating member to form a disc shaped detection liquid membrane locally in the gap, proximate to and including said center of rotation; and b) an acoustic emission sensor (43) integrally affixed to said detection liquid supply unit for detecting ultrasonic vibrations or acoustic emissions transmitted through the detection liquid membrane formed in the gap, and vibrations or emissions generated by physical contact between the rotating member and the workpiece, c) wherein a recess (48) is formed in the end face of said rotating member at the center of rotation of said member and facing said liquid supply unit, thereby trapping the detection liquid membrane in said recess.

3. An ultrasonic detection apparatus (41) for detecting physical contact between a rotating member (21, 31) and a workpiece, comprising:

a) a detection liquid supply unit (42) having a planar end surface disposed closely adjacent a planar end face portion of said rotating member so as to form a small, planar, uniformly wide gap (S) therebetween, for supplying a detection liquid directly through a central portion of said planar end surface to a center of rotation of said rotating member to form a disc shaped detection liquid membrane locally in the gap, proximate to and including said center of rotation; and b) an acoustic emission sensor (43) integrally affixed to said detection liquid supply unit for detecting ultrasonic vibrations or acoustic emissions transmitted through the detection liquid membrane formed in the gap, and vibrations or emissions generated by physical contact between the rotating member and the workpiece, c) wherein the detection liquid is supplied to the rotating member through a feed hole (45) in the supply unit, and a diameter d of the feed hole and a width w of the gap satisfy the following expression:

$$\pi d^2/4 > \pi dw.$$

4. The ultrasonic detection apparatus as claimed in claim 2, wherein said detection liquid supply unit has an air path (49) formed to face a peripheral surface of said recess and through which air is introduced and blown out to a peripheral surface of said recess to further trap the detection liquid in said recess.

5. The ultrasonic detection apparatus as claimed in claim 2, wherein said rotating member has a shaft which is exposed from said recess and on which the detection liquid membrane is formed, so that ultrasonic vibrations of said shaft are detected by said sensor.

6. The ultrasonic detection apparatus as claimed in claim 1, wherein said detection liquid supply unit has a detection plate (44), and said detection liquid is supplied through said detection plate.

7. The ultrasonic detection apparatus as claimed in claim 2, wherein said detection liquid supply unit has a detection plate (44) inserted into the recess, the detection liquid is supplied to the rotating member through a feed hole (45) in the detection plate, and a diameter d of the feed hole, a width w of the gap, a diameter $d_1$ of the detection plate and a diameter $d_2$ of the recess satisfy the following expression:

$$\pi d^2/4 > \pi dw > (\pi d_2^2 - \pi d_1^2)/4.$$

* * * * *